(12) United States Patent
de la Rama et al.

(10) Patent No.: US 11,457,974 B2
(45) Date of Patent: *Oct. 4, 2022

(54) CATHETER HAVING FLEXIBLE TIP WITH MULTIPLE FLEXIBLE SEGMENTS

(71) Applicant: St. Jude Medical, Atrial Fibrillation Division, Inc., St. Paul, MN (US)

(72) Inventors: Alan de la Rama, Cerritos, CA (US); Cary Hata, Irvine, CA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/148,873

(22) Filed: Oct. 1, 2018

(65) Prior Publication Data

US 2019/0099585 A1 Apr. 4, 2019
US 2019/0275291 A2 Sep. 12, 2019

Related U.S. Application Data

(63) Continuation of application No. 13/704,619, filed as application No. PCT/US2011/040781 on Jun. 16, 2011, now Pat. No. 10,118,015.

(Continued)

(51) Int. Cl.
*A61B 18/14* (2006.01)
*A61M 25/00* (2006.01)
*A61B 18/00* (2006.01)

(52) U.S. Cl.
CPC ..... *A61B 18/1492* (2013.01); *A61M 25/0052* (2013.01); *A61B 2018/00404* (2013.01);
(Continued)

(58) Field of Classification Search
CPC .......... A61M 25/0052; A61B 18/1492; A61B 2018/00821; A61B 2018/00869;
(Continued)

(56) References Cited

U.S. PATENT DOCUMENTS 4,325,374 A  4/1982 Komiya
5,279,299 A  1/1994 Imran
(Continued)

FOREIGN PATENT DOCUMENTS

CN  1897885 A  1/2007
JP  3162588 B2  5/2001
(Continued)

OTHER PUBLICATIONS

International Search Report and Written Opinion, PCT/US2011/040781 dated Nov. 25, 2011.
(Continued)

*Primary Examiner* — Tiffany Legette
(74) *Attorney, Agent, or Firm* — Armstrong Teasdale LLP

(57) ABSTRACT

A catheter apparatus includes an elongated body having a distal portion including a distal end, a plurality of flexible segments, and at least one intermediate segment that is less flexible than the flexible segments. Adjacent flexible segments are spaced from each other longitudinally by the at least one intermediate segment. Each of the flexible segments include a sidewall having at least one elongated gap extending at least partially therethrough and forming interlocking members. The at least one intermediate segment is shorter than the flexible segments.

19 Claims, 4 Drawing Sheets

Related U.S. Application Data

(60) Provisional application No. 61/355,242, filed on Jun. 16, 2010.

(52) U.S. Cl.
CPC .............. *A61B 2018/00434* (2013.01); *A61B 2018/00511* (2013.01); *A61B 2018/00821* (2013.01); *A61B 2018/00869* (2013.01); *A61B 2018/00875* (2013.01); *A61B 2018/1407* (2013.01)

(58) Field of Classification Search
CPC .. A61B 2018/1407; A61B 2018/00404; A61B 2018/00434; A61B 2018/004504; A61B 2018/00511; A61B 2018/00875
See application file for complete search history.

(56) References Cited

U.S. PATENT DOCUMENTS

| | | | |
|---|---|---|---|
| 5,364,352 A | 11/1994 | Cimino et al. | |
| 5,378,230 A | 1/1995 | Mahurkar | |
| 5,462,521 A | 10/1995 | Brucker et al. | |
| 5,487,385 A | 1/1996 | Avitall | |
| 5,520,682 A | 5/1996 | Baust et al. | |
| 5,545,200 A | 8/1996 | West et al. | |
| 5,569,220 A | 10/1996 | Webster, Jr. | |
| 5,643,197 A | 7/1997 | Brucker et al. | |
| 5,772,642 A | 6/1998 | Ciamacco, Jr. et al. | |
| 5,800,428 A | 9/1998 | Nelson et al. | |
| 5,810,802 A | 9/1998 | Panescu et al. | |
| 5,833,632 A | 11/1998 | Jacobsen et al. | |
| 5,853,425 A | 12/1998 | Houser | |
| 5,893,885 A | 4/1999 | Webster, Jr. | |
| 5,919,188 A | 7/1999 | Shearon et al. | |
| 5,951,471 A | 9/1999 | de la Rama et al. | |
| 5,954,719 A | 9/1999 | Chen et al. | |
| 5,992,418 A | 11/1999 | de la Rama et al. | |
| 6,001,095 A | 12/1999 | de la Rama et al. | |
| 6,010,500 A | 1/2000 | Sherman et al. | |
| 6,030,382 A | 2/2000 | Fleischman et al. | |
| 6,063,080 A | 5/2000 | Nelson et al. | |
| 6,210,409 B1 | 4/2001 | Ellman et al. | |
| 6,217,573 B1 | 4/2001 | Webster | |
| 6,233,476 B1 | 5/2001 | Strommer et al. | |
| 6,235,022 B1 | 5/2001 | Hallock et al. | |
| 6,251,134 B1 | 6/2001 | Alt et al. | |
| 6,273,876 B1 | 8/2001 | Klima et al. | |
| 6,308,090 B1 | 10/2001 | Tu et al. | |
| 6,325,797 B1 | 12/2001 | Stewart et al. | |
| 6,332,880 B1 | 12/2001 | Yang et al. | |
| 6,346,104 B2 | 2/2002 | Daly et al. | |
| 6,356,790 B1 | 3/2002 | Maguire et al. | |
| 6,379,349 B1 | 4/2002 | Muller et al. | |
| 6,405,067 B1 | 6/2002 | Mest et al. | |
| 6,463,632 B2 | 10/2002 | Craig, Jr. | |
| 6,464,632 B1 | 10/2002 | Taylor | |
| 6,493,590 B1 | 12/2002 | Wessman et al. | |
| 6,498,944 B1 | 12/2002 | Ben Haim et al. | |
| 6,522,930 B1 * | 2/2003 | Schaer | A61B 18/1492 606/41 |
| 6,604,003 B2 | 8/2003 | Fredricks et al. | |
| 6,611,699 B2 | 8/2003 | Messing | |
| 6,690,963 B2 | 2/2004 | Ben Haim et al. | |
| 6,780,183 B2 | 8/2004 | Jimenez, Jr. et al. | |
| 6,788,967 B2 | 9/2004 | Ben Haim et al. | |
| 6,921,397 B2 | 7/2005 | Corcoran et al. | |
| 6,980,843 B2 | 12/2005 | Eng et al. | |
| 7,013,169 B2 | 3/2006 | Bowe | |
| 7,137,395 B2 | 11/2006 | Fried et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,389,148 B1 | 6/2008 | Morgan | |
| 7,416,552 B2 | 8/2008 | Paul et al. | |
| 7,468,027 B2 | 12/2008 | Barbut et al. | |
| 7,536,218 B2 | 5/2009 | Govari et al. | |
| 7,537,595 B2 | 5/2009 | McClurken | |
| 7,565,208 B2 | 7/2009 | Harris et al. | |
| 7,669,309 B2 | 3/2010 | Johnson et al. | |
| 7,699,771 B2 | 4/2010 | Wendlandt | |
| 7,706,891 B2 | 4/2010 | Hastings et al. | |
| 7,824,517 B2 | 11/2010 | Kampa et al. | |
| 7,826,881 B1 | 11/2010 | Beatty et al. | |
| 2001/0007070 A1 | 7/2001 | Stewart et al. | |
| 2001/0012956 A1 | 8/2001 | Behl et al. | |
| 2002/0058866 A1 | 5/2002 | Segner et al. | |
| 2002/0072710 A1 | 6/2002 | Stewart et al. | |
| 2003/0125730 A1 | 7/2003 | Berube et al. | |
| 2004/0015215 A1 | 1/2004 | Fredricks et al. | |
| 2004/0034348 A1 | 2/2004 | Rashidi | |
| 2004/0064158 A1 * | 4/2004 | Klein | A61N 1/056 607/9 |
| 2004/0143256 A1 | 7/2004 | Bednarek | |
| 2004/0193239 A1 | 9/2004 | Falwell et al. | |
| 2004/0204671 A1 | 10/2004 | Stubbs et al. | |
| 2004/0220461 A1 | 11/2004 | Schwartz | |
| 2004/0231683 A1 | 11/2004 | Eng et al. | |
| 2004/0243143 A1 | 12/2004 | Corcoran et al. | |
| 2004/0267106 A1 | 12/2004 | Segner et al. | |
| 2005/0004563 A1 | 1/2005 | Racz et al. | |
| 2005/0043713 A1 | 2/2005 | Zhou | |
| 2005/0054989 A1 | 3/2005 | McGuckin et al. | |
| 2005/0070894 A1 * | 3/2005 | McClurken | A61B 18/1492 606/48 |
| 2005/0143729 A1 | 6/2005 | Francischelli et al. | |
| 2005/0187561 A1 | 8/2005 | Lee Sepsick et al. | |
| 2005/0197633 A1 | 9/2005 | Schwartz et al. | |
| 2005/0272975 A1 | 12/2005 | McWeeney et al. | |
| 2006/0004353 A1 | 1/2006 | Koyfman et al. | |
| 2006/0064123 A1 | 3/2006 | Bonnette et al. | |
| 2006/0149192 A1 * | 7/2006 | Deniega | A61M 25/0069 604/264 |
| 2006/0200191 A1 | 9/2006 | Zadno Azizi | |
| 2006/0287650 A1 | 12/2006 | Cao et al. | |
| 2007/0005053 A1 | 1/2007 | Dando | |
| 2007/0156114 A1 | 7/2007 | Worley et al. | |
| 2007/0179491 A1 | 8/2007 | Kratoska et al. | |
| 2007/0299424 A1 | 12/2007 | Cumming et al. | |
| 2008/0091195 A1 | 4/2008 | Sliwa et al. | |
| 2008/0125772 A1 * | 5/2008 | Stone | A61B 18/1492 606/41 |
| 2008/0139999 A1 | 6/2008 | Gibson et al. | |
| 2008/0161788 A1 | 7/2008 | Dando et al. | |
| 2008/0161789 A1 | 7/2008 | Thao et al. | |
| 2008/0249522 A1 | 10/2008 | Pappone et al. | |
| 2008/0275428 A1 | 11/2008 | Tegg et al. | |
| 2008/0281319 A1 | 11/2008 | Paul et al. | |
| 2008/0294158 A1 * | 11/2008 | Pappone | A61B 18/1492 606/41 |
| 2008/0300589 A1 | 12/2008 | Paul et al. | |
| 2008/0312713 A1 | 12/2008 | Wilfley et al. | |
| 2009/0012517 A1 | 1/2009 | de la Rama et al. | |
| 2009/0228092 A1 | 9/2009 | Raeder-Devens et al. | |
| 2009/0247993 A1 | 10/2009 | Kirschenman et al. | |
| 2009/0287210 A1 | 11/2009 | Kauphusman et al. | |
| 2010/0152731 A1 | 6/2010 | de la Rama et al. | |
| 2010/0174177 A1 | 7/2010 | Wu | |
| 2010/0286684 A1 * | 11/2010 | Hata | A61B 18/1492 606/33 |
| 2011/0118582 A1 | 5/2011 | De la Rama et al. | |

FOREIGN PATENT DOCUMENTS

| | | |
|---|---|---|
| JP | 2006509547 A | 3/2006 |
| JP | 2002513652 A5 | 6/2006 |
| JP | 2008136875 A | 6/2008 |
| JP | 2008541799 A5 | 5/2009 |
| JP | 2010533564 A5 | 8/2011 |
| WO | 1995010327 A1 | 4/1995 |
| WO | 1996034652 A1 | 11/1996 |
| WO | 1997017904 A1 | 5/1997 |
| WO | 1999056812 A2 | 11/1999 |

(56) References Cited

FOREIGN PATENT DOCUMENTS

| WO | 2002087453 | A1 | 11/2002 |
| WO | 2005094661 | A1 | 10/2005 |
| WO | 2007035554 | A1 | 3/2007 |
| WO | 2008124619 | A1 | 10/2008 |
| WO | 2008147599 | A1 | 12/2008 |
| WO | 2009120982 | A2 | 10/2009 |
| WO | 2010129661 | A1 | 11/2010 |

OTHER PUBLICATIONS

International Search Report and Written Opinion, PCT/US2011/046266 dated Dec. 7, 2011.
H. Krum et al., "Catheter-based renal sympathetic denervation for resistant hypertension: a multicentre safety and proof-of-principle cohort study", www.thelancet.com, Mar. 30, 2009, pp. 1-7.
PCT International Search Report (PCT/US2008/069248), dated Jan. 15, 2009, 2 pages.

* cited by examiner

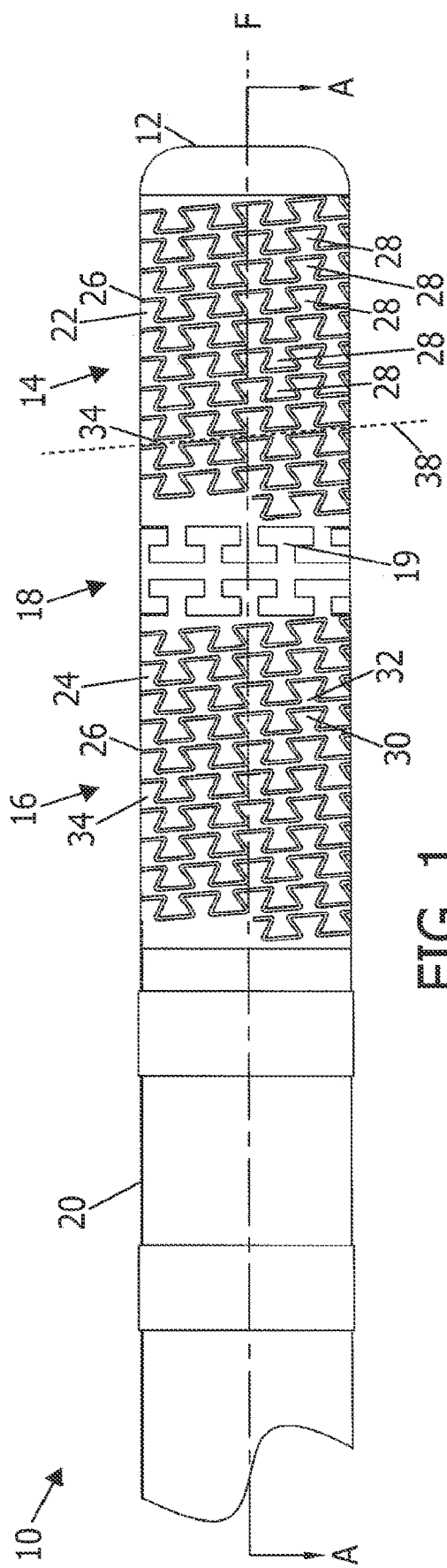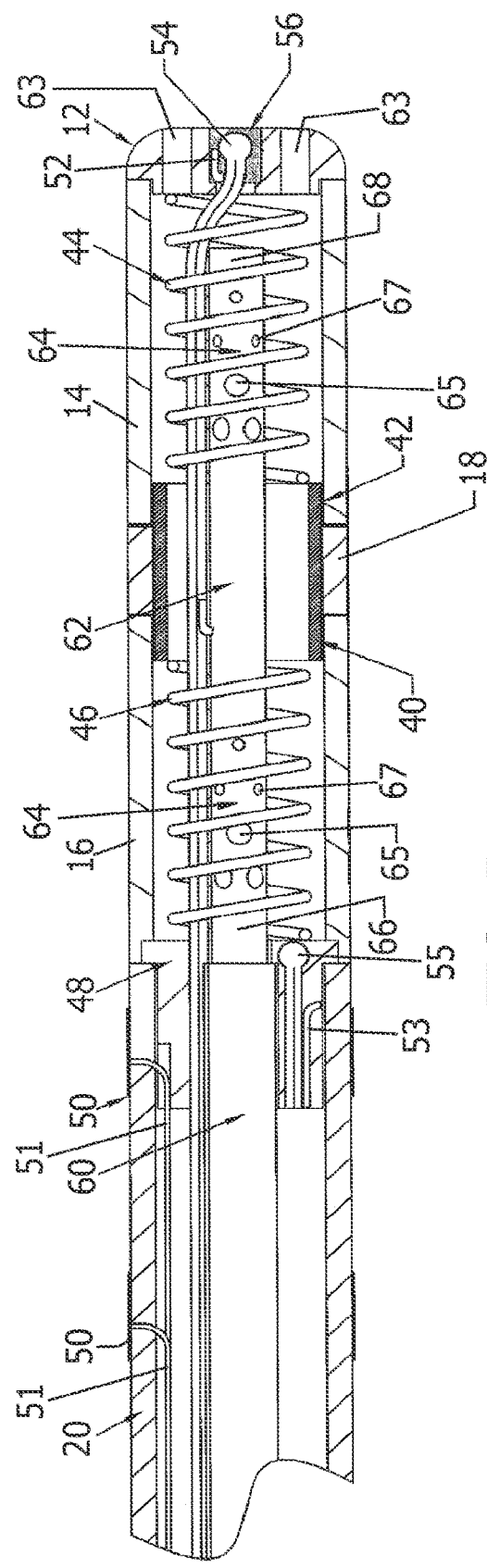

CATHETER HAVING FLEXIBLE TIP WITH MULTIPLE FLEXIBLE SEGMENTS

CROSS REFERENCE TO RELATED APPLICATIONS

This patent application is a Continuation of U.S. patent application Ser. No. 13/704,619 filed Dec. 16, 2012, issued as U.S. Pat. No. 10,118,015, which is a National Stage Entry of PCT/US2011/040781 filed Jun. 16, 2011, which claims the benefit of U.S. Provisional Application No. 61/355,242 filed Jun. 16, 2010. The '015 patent, the '781 application, and the '242 application are hereby incorporated by reference as though fully set forth herein.

BACKGROUND OF THE INVENTION

The field of the invention relates generally to catheters and more particularly to catheters having flexible tips and including multiple flexible segments.

Catheters are flexible, tubular devices that are widely used by physicians performing medical procedures to gain access into interior regions of the body. Some known catheters include electrodes that are used for electrically mapping a body part and/or delivering therapy to an area of the body. These types of catheters perform best when the electrode has good and sufficient contact with the tissue that is being treated. It is also advantageous that the catheter not inadvertently damage tissue while it is inside the body.

BRIEF DESCRIPTION OF THE INVENTION

In one aspect, a catheter apparatus includes an elongated body having a distal portion including a distal end, a plurality of flexible segments, and at least one intermediate segment that is less flexible than the flexible segments. Adjacent flexible segments are spaced from each other longitudinally by the at least one intermediate segment. Each of the flexible segments includes a sidewall having at least one elongated gap extending at least partially therethrough and forming interlocking members. The at least one intermediate segment is shorter than the flexible segments.

In another aspect, a distal portion for a catheter includes a distal end, a plurality of flexible segments, and at least one intermediate segment. Adjacent flexible segments are spaced from each other longitudinally by the at least one intermediate segment. Each flexible segment includes a sidewall having at least one elongated gap extending at least partially therethrough and forming interlocking members. The at least one intermediate segment is shorter than the flexible segments. The elongated gaps impart flexibility to the flexible segments and enable different operating configurations relative to a longitudinal axis.

BRIEF DESCRIPTION OF THE DRAWINGS

FIG. 1 is a schematic view of a distal portion of an ablation catheter according to one embodiment of the invention.

FIG. 5 is a partial cross-sectional view of the distal portion of the ablation catheter shown in FIG. 1.

DETAILED DESCRIPTION OF THE INVENTION

Figure 2:
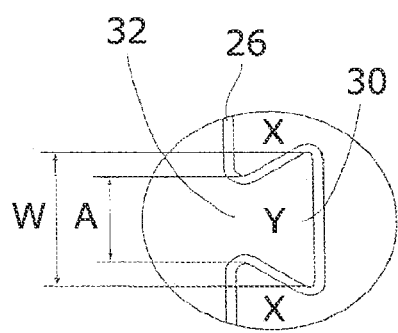
FIG. 2 is an expanded view of an interlocking pattern formed by channels in the catheter shown in FIG. 1.

The invention can now be better understood by turning to the following detailed description of numerous embodiments, which are presented as illustrated examples of the invention defined in the claims. It is expressly understood that the invention as defined by the claims may be broader than the illustrated embodiments described below.

Embodiments of ablation catheters having tips including flexible and bendable electrodes, and also freedom of movement to shorten an axial length of the catheter tip, while reliably creating linear lesions in body tissues are described. The flexibility of the electrodes increases an electrode-to-tissue contact area, and in turn improves ablation of tissue. Especially in tissue where ridges are present, the flexible tip electrodes can be dragged across the ridges with improved continuous electrode-to-tissue contact.

These and other benefits are accomplished by providing a flexible distal portion for a catheter that includes a plurality of flexible segments that each include a generally hollow cylindrical structure having an interior lumen. A rounded distal end may be provided. The cylindrical wall of the flexible segment may have a variety of different types of channels or elongated grooves defining gaps in the cylindrical wall and imparting some flexibility thereto, including flexing and bending capability. In some embodiments, the catheter is an ablation catheter and the flexible segments are electrodes. This flexibility allows the flexible electrodes to conform to and establish sufficient surface contact with body tissues that may have irregular surface area including ridges and the like, and tissues that may be contracting and stretching, or moving, to more reliably create linear lesions on the body tissue. The electrodes also are configured to provide a freedom of movement and shortening of a length of the catheter tip along its longitudinal axis to maintain surface contact with, for example, contracting and stretching, or moving tissue that is targeted for ablation. The channels, grooves, and associated elongated gaps may have various shapes, sizes and overall configurations as explained below in numerous exemplary embodiments.

FIG. 1 is a schematic view of a distal portion 10 of an ablation catheter according to one embodiment of the invention. Distal portion 10 includes a flat distal end 12 that is substantially circular and has a rounded edge at its perimeter. In an alternative embodiment, distal end 12 is domed shaped and has a curved distal end. In another embodiment, distal end 12 is oval or elliptical shaped. Distal portion 10 also includes a distal flexible segment 14 and a proximal flexible segment 16. Flexible segments 14, 16 are separated by an intermediate segment 18. In one embodiment, flexible segments 14, 16 are electrodes and intermediate segment 18 is a nonconductive member, and intermediate segment 18 is less flexible than flexible segments 14, 16. In an alternative embodiment, intermediate segment 18 is as flexible as flexible segments 14, 16. Distal flexible segment 14 is coupled to distal end 12 and to intermediate segment 18.

Proximal flexible segment 16 is coupled to intermediate segment 18 and a catheter shaft 20.

Non-conductive intermediate segment 18 electrically isolates flexible electrode segments 14, 16 and secures flexible electrode segments 14, 16 thereto. As seen in FIG. 1, intermediate segment 18 has T-shaped protrusions 19 that match and fit within corresponding T-shaped voids or cavities on the edges of flexible electrode segments 14, 16 to form interlocking connections that couple flexible electrode segments 14, 16 to intermediate segment 18. Of course, other configurations can be used to form the connections as long as electrode segments 14, 16 are secured to intermediate section 18. In one embodiment non-conductive intermediate segment 18 is made of polyimide or some other nonconductive material. It may be formed as a strip and then bent into a tubular shape to form the interconnecting coupling between flexible electrode segments 14, 16. The length of intermediate segment 18 is sufficiently small to allow the ablation zones of flexible electrode segments 14, 16 to overlap and form a continuous lesion. The short length of intermediate segment 18 also preserves the overall flexibility of distal portion 10 by limiting the size of intermediate segment 18, which is non-flexible or at least not as flexible as electrode segments 14, 16. In one example, flexible electrode segments 14, 16 are each about 4 mm in length while intermediate segment 18 is about 1 mm in length. Typically, intermediate segment 18 is substantially shorter in length than flexible electrode segments 14, 16 (e.g., preferably less than a half, more preferably less than a third, and most preferably less than a fourth).

Distal flexible electrode segment 14 includes a cylindrical sidewall 22 and proximal flexible electrode segment 16 includes a cylindrical sidewall 24. Sidewalls 22, 24 have helical or spiral channels or grooves 26 cut or otherwise formed entirely through sidewalls 22, 24 to create elongated gaps or openings. As used herein, an elongated opening preferably has a length that is at least about 3 times the width of the opening, more preferably at least about 5 times, and most preferably at least about 10 times.

In an alternative embodiment, sidewalls 22, 24 include helical or spiral channels or grooves forming elongated gaps or openings that do not extend entirely through sidewalls 22, 24. Channels or grooves 26 that do not extend entirely through sidewalls 22, 24, define elongated openings of decreased wall thickness and decreased cross-sectional area of sidewalls 22, 24 and hence the areas of the wall that include channels 26 are structurally weaker and less rigid than areas of sidewalls 22, 24 where the elongated openings are not present, imparting flexible properties to the electrode wall. As used herein, an elongated opening preferably has a length that is at least about 3 times the width of the groove, more preferably at least about 5 times, and most preferably at least about 10 times. As can be appreciated, channels 26 extending completely through electrode sidewalls 22, 24 will generally impart more flexibility, or less rigidity, to sidewalls 22, 24 than will channels 26 that do not extend entirely through sidewalls 22, 24.

In a further alternative embodiment, the channels extend in a circular and planar configuration, with each channel being equidistant from adjacent channels. In additional embodiments, the channels have a non-planar helical configuration that completes more or less than one 360 degree loop or turn on the surface of the electrode sidewall. Each of these channels has discrete end points and each electrode includes multiple channels.

In another embodiment, the electrode may include annular rings extending in a plane that do not form a continuous unending loop, but rather channels forming loops having two terminal ends that are spaced apart from one another. A further embodiment may include a combination of continuous and non-continuous, planar and non-planar channel configurations.

As shown in FIG. 1, channels 26 each form interlocking members and create an interlocking pattern that follows a continuous helical path configuration from one end of flexible segment 14 to the other and from one end of flexible segment 16 to the other. Channels 26 outline alternating interlocking members, or blocks 28.

Blocks 28 are disposed on both sides of channel 26. Each block 28 has a head 30 and a neck 32, wherein head 30 is wider than neck 32. As shown in FIG. 2, an interlocking pattern includes a first head, represented by "Y", which has a neck 32 situated on one side of channel 26, disposed between second and third heads, represented by "X". Second and third heads X each have necks situated on the other side of channel 26 and on opposite sides of head Y. Adjacent blocks 28 are interlocked because head 30 is wider than adjacent necks 32 and is therefore locked between adjacent necks 32. For example, second and third heads X in FIG. 2 are separated by a shortest distance A in FIG. 2, and distance A is shorter than a width W of the head Y, thereby restricting relative movement of two adjacent loops away from each other and preventing adjacent blocks 28 from separating.

Figure 3:
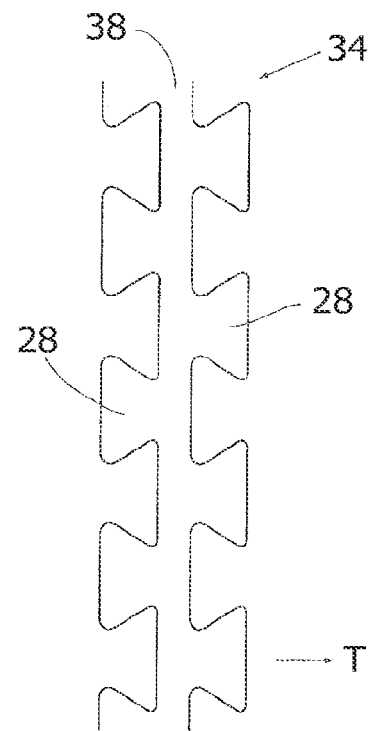
FIG. 3 illustrates a stem member including interlocking members formed by the channels shown in FIG. 2.

Contemplated patterns of elongated openings can also be described according to structures of sidewalls 22, 24, instead of the shape of channel 26. For example, FIG. 3 illustrates an electrode wall including a stem member 34 that helically extends about a longitudinal axis of the electrode forming a series of stem loops (see FIG. 1). Stem member 34 includes a plurality of protruding blocks 28 peripherally disposed on both sides of stem member 34. Each block 28 transversely extends in a lateral direction indicated by arrow T in FIG. 3 toward an adjacent stem loop in electrode sidewall 22 shown in FIG. 1. Each adjacent stem member 34 includes blocks 28 that are staggered from blocks 28 in immediately adjacent stem members, resulting in an interlocking block pattern. Blocks 28 extending from stem member 34 can have various shapes. For example, at least some blocks 28 may have a shape of an upside down triangle as illustrated, where one angle of the triangle represents the neck region.

Figure 4:
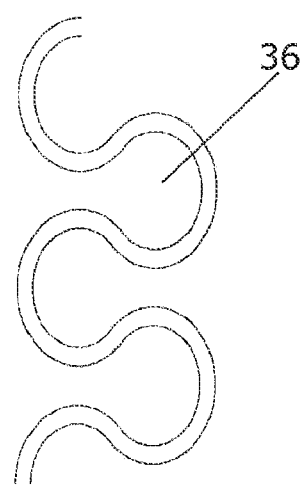
FIG. 4 illustrates an alternative interlocking pattern having rounded members.

FIG. 4 illustrates an alternative embodiment having alternatively shaped blocks 36 having a rounded bulbous shape. Contemplated heads of the bulbous protrusions are wider than their corresponding necks, facilitating an interlocking block pattern.

Referring back to FIGS. 1 and 3, stem members 34 have an axis 38 that extends in a helix about a longitudinal axis F with a pitch between and including 0.5 to 10 degrees. Channels 26 between blocks 28 of stem members 34 improve a flexibility of flexible segments, or electrodes, 14, 16, and allow electrodes 14, 16 to flex and bend along their longitudinal length and relative to the catheter body to which they are attached. For example, the ability of electrodes 14, 16 to flex allows an approximately 4 mm length of a respective electrode 14, 16 to bend between and including 0.2 degrees to 70 degrees relative to the longitudinal axis from a substantially straight position. More specifically, the ability to flex allows an approximately 4 mm electrode length to bend between and including 5 degrees to 50 degrees relative to the longitudinal axis from a substantially straight position. Even more specifically, the ability to flex allows an approximately 4 mm electrode length to bend about 20 to 22 degrees relative to the longitudinal axis from a substantially straight position and, accordingly, distal portion 10 which has two 4 mm electrodes 14, 16 will bend approximately 40 to 44 degrees.

The ability of electrodes 14, 16 to flex provides better contact with the target tissue, for example, in the trabeculated endocardial tissue where there are valleys, ridges, and pockets in the tissue surface. Electrode-to-tissue contact area is increased by using sidewalls 22, 24 of electrodes 14, 16, respectively, to deliver energy for ablation. The increased contact surface increases the likelihood of creating larger lesions at a given contact force and power setting. This in turn enables deeper ablation without having to increase the power setting, which is beneficial because increased power settings may undesirably increase the likelihood of coagulation.

Flexible electrodes 14, 16 are configured to absorb contraction and stretching of tissue, and improve continuous tissue contact in a beating heart during systole and diastole, whether electrodes 14, 16 contact the tissue in a parallel, perpendicular, or other orientation. Continuous tissue contact is also maintained regardless of whether the electrode is stationary at one location or when the electrode is in motion and being dragged. Without such flexibility, a standard rigid tip electrode would "jump off" of the tissue in response to a beating heart.

Alternative embodiments of flexible electrodes for catheters include physiologic-sensing capability to measure different aspects of the body. Such capability is obtained by using one or more sensors located at distal portion 10 of the catheter. Such a sensor may be disposed within the hollow electrode to measure one or more physiologic aspects related to a procedure. Such data can be collected and monitored by the operator during the procedure.

Unlike known elongated electrodes (e.g., U.S. Pat. No. 6,063,080), which can be laid across a tissue to create relatively long linear lesions, the flexible electrodes as described have the unexpected advantage of improving precision in mapping and control at specific locations within the heart for more precise ablation, especially in relatively tight anatomical structures. Known elongated electrodes have difficulty positioning in such tight anatomical structures.

One unexpected advantage achieved with a flexible tip electrode is minimized "flipping." When a standard rigid tip electrode is manipulated within a body cavity having valleys and pockets in the tissue, the tip electrode can get caught or stuck in the tissue. As a physician continues to apply force in an attempt to move the tip electrode even though it is caught or stuck, the tip electrode may suddenly "flip" out of the tissue. Such "flipping" is highly undesirable and should be avoided. The proposed flexible tip electrodes greatly minimize "flipping" issues, and allow smoother dragging and motion across valleys and pockets in target tissue. In addition, one or more pulling wires (not shown) can be utilized with distal portion 10. In one embodiment, pulling wires are anchored to distal end 12 and extend through a proximal end of the catheter such that an operator can manipulate distal portion 10 of the catheter. In an alternative embodiment, a distal end of the pulling wire is connected to the catheter at a location other than distal end 12. The pulling wires allow the operator to configure distal portion 10 in different directions and curvatures during insertion of the catheter as well as during the procedure. In one embodiment, the pulling wires are anchored as traditionally known in the art and may extend through the catheter wall or may extend through a lumen. Multiple wires may be anchored at set lengths from distal end 12 in pairs on opposite sides of the catheter, or the anchor points may be offset and thus allow for asymmetric curvatures and sweep.

FIG. 5 is a partial cross-sectional view of distal portion 10 of the ablation catheter of FIG. 1. A tube 40 is disposed internally between flexible electrode segments 14, 16, and is attached to flexible electrode segments 14, 16 by an adhesive 42 or the like. In one embodiment, tube 40 is fabricated from a PEEK tube. In an alternative embodiment tube 40 is fabricated from other suitable nonconductive materials. A distal spring coil 44 extends between distal end 12 and tube 40. A proximal spring coil 46 extends between tube 40 and a tip stem 48 and is attached to proximal electrode segment 16 and catheter shaft 20. Spring coils 44, 46 bias flexible electrode segments 14, 16 to stretch lengthwise. Spring coils 44, 46 provide resilient biasing supports for flexible electrode segments 14, 16, respectively, both when sidewalls 22, 24 have channels 26 extending completely therethrough and when sidewalls 22, 24 have channels that do not extend completely therethrough. Spring coils 44, 46 provide structural integrity to sidewalls 22, 24, respectively, and resiliently maintain flexible electrode segments 14, 16 in a pre-determined configuration when no applied force is placed on distal portion 10. In an alternative embodiment, biasing members other than spring coils can be used to bias electrode segments 14, 16 to stretch lengthwise. As shown in FIG. 5, the pre-determined electrode configuration at rest orients the longitudinal axis of each flexible electrode segment 14, 16 along a straight line. In a different embodiment, the pre-determined configuration at rest may orient the longitudinal axes of electrode segments 14, 16 along a curved or arcuate path. Such a configuration may be imparted to distal portion 10 through use of suitable shape memory alloys.

Channels 26 that extend entirely through electrode sidewalls 22, 24 provide a sufficient gap in sidewalls 22, 24 to allow shortening of a length of electrode segments 14, 16 when a sufficient force is applied to the electrode. As explained above, channel 26 extends, for example, between a head 30 and a neck 32 of an adjacent loop in electrode sidewalls 22, 24, and allows a freedom of movement between adjacent stems along the longitudinal axis of the electrode wall when channel 26 is narrowed or closed. Likewise, channel 26 between adjacent heads 30 provides a freedom of movement for lengthening of electrode sidewalls 22, 24 along the longitudinal length of electrode flexible segments 14, 16 when channel 26 is opened or widened. Such shortening or lengthening may involve widening or narrowing one or more channels 26 in the various embodiments described above.

In an exemplary embodiment, flexible electrode segments 14, 16 can shorten between and including 0.2% to 10% of an axial resting length of flexible electrode segments 14, 16 when channels 26 in electrode sidewalls 22, 24 are closed. In one embodiment, channels 26 in electrode sidewalls 22, 24 allow shortening of the axial length between and including 0.1% to 8% of the resting length. More specifically, channels 26 in electrode sidewalls 22, 24 allow axial shortening of the length between and including 0.5% to 5% of the resting length, and even more specifically, channels 26 in electrode sidewalls 22, 24 allow shortening of the resting length between and including 0.1% to 0.5% of the length.

In one embodiment, an at rest electrode segment 14, 16, assumes a pre-determined shape stretching in the longitudinal direction and opening channels 26 a predetermined amount. When electrode segments 14, 16 contact tissue, an applied compressive force causes channels 26 to narrow or close and electrode segments 14, 16 shorten against the force. Once shortened, the width of channels 26 is decreased and may fully close such that the length of electrode segments 14, 16 reach a minimum axial length that is substantially unaffected by further exertion of applied force.

In the exemplary embodiment, spring coils 44, 46, or flexible electrodes 14, 16, or any combination thereof, may be, and in one embodiment is, fabricated from biocompatible materials that are suitable for ablation temperatures. Such materials include, without limitation, natural and synthetic polymers, various metals and metal alloys, Nitinol, naturally occurring materials, textile fibers, and combinations thereof. In the exemplary embodiment, distal portion 10, and other catheter components including, without limitation, flexible segments 14, 16 and coils 44, 46, are fabricated from a substantially or entirely non-magnetic, non-electrically conductive, and non-RF reactive material to enable magnetic resonance imaging (MRI) of distal portion 10 using an MRI system (not shown) for positioning and/or orienting distal portion 10. While the above described catheter is advantageous for use with an MRI system, it is contemplated that magnetic fields and gradients to generate images of distal portion 10 may alternatively be generated by other systems and techniques if desired. For example, in one embodiment, all, or a portion of, distal portion 10 is fabricated from 90% platinum and 10% iridium, or other materials known in the art, such that all or part of distal portion 10 is viewable under fluoroscopic exposure.

Additionally or alternatively, distal portion 10 may include and/or be coated with a conductive material including, without limitation, gold and/or platinum, to increase a thermal conductivity of the electrodes. Moreover, distal portion 10 can be and, in one embodiment, is coated with heparin to provide an anticoagulation effect. Furthermore, distal portion 10 can be and, in one embodiment, is electropolished to reduce sharp edges.

In a further alternative embodiment, the catheter can be used with an electric field-based system, such as, for example, the EnSite NavX™ system commercially available from St. Jude Medical, Inc., and as generally shown with reference to U.S. Pat. No. 7,263,397 entitled "Method and Apparatus for Catheter Navigation and Location and Mapping in the Heart," the disclosure of which is incorporated herein by reference in its entirety. In other embodiments, the catheter can be used with systems other than electric field-based systems. For example, a magnetic field-based system such as the Carto™ system commercially available from Biosense Webster, and as generally shown with reference to one or more of U.S. Pat. No. 6,498,944 entitled "Intrabody Measurement;" U.S. Pat. No. 6,788,967 entitled "Medical Diagnosis, Treatment and Imaging Systems;" and U.S. Pat. No. 6,690,963 entitled "System and Method for Determining the Location and Orientation of an Invasive Medical Instrument," the disclosures of which are incorporated herein by reference in their entireties. In other embodiments, the catheter can be used with a magnetic field-based system such as the gMPS system commercially available from MediGuide Ltd., and as generally shown with reference to one or more of U.S. Pat. No. 6,233,476 entitled "Medical Positioning System;" U.S. Pat. No. 7,197,354 entitled "System for Determining the Position and Orientation of a Catheter;" and U.S. Pat. No. 7,386,339 entitled "Medical Imaging and Navigation System," the disclosures of which are incorporated herein by reference in their entireties. In yet another embodiment, the catheter can be used with a combination electric field-based and magnetic field-based system, such as, for example and without limitation, the Carto 3™ system also commercially available from Biosense Webster, and as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the catheter can be used in conjunction with other commonly available systems, such as, for example and without limitation, fluoroscopic, computed tomography (CT), and magnetic resonance imaging (MRI)-based systems. In these embodiments, the catheter includes one or more tracking elements that enable the location of the catheter to be tracked. Such tracking elements can include active and/or passive elements such as sensors and/or electrodes.

As seen in FIGS. 1 and 5, a pair of band electrodes 50 is provided on catheter shaft 20 and may be used for diagnostic purposes or the like. A pair of electrode wires 51 extends to band electrodes 50 and provides energy to band electrodes 50. Distal portion 10 also includes conductor wires 52, 53 and thermocouples 54, 55. An adhesive 56, such as urethane, maintains conductor wire 52 and thermocouple 54 in place at distal end 12. In one embodiment, distal end 12 is in electrical and thermal contact with distal flexible electrode segment 14. Conductor wire 53 and thermocouple 55 are coupled to tip stem 48 and held in place with an adhesive, such as urethane. In one embodiment, tip stem 48 is in electrical and thermal contact with proximal flexible electrode segment 16. Conductor wires and thermocouples may also be provided at other locations at or near other electrodes or electrode segments. Wires 51, 52, 53 are coupled at their proximal end to an energy source as is well known in the art. In addition, thermocouples 54, 55 are coupled to an energy source at their proximal end as is well known in the art. Accordingly, flexible electrodes 14, 16 can be energized sequentially or simultaneously. In one embodiment, distal portion 10 can be operated in a temperature control mode and/or in a power control mode. In an alternative embodiment, distal end 12 is unitary with flexible electrode segment 14 and tip stem 48 is unitary with proximal flexible electrode segment 16.

Catheters having flexible tip electrodes such as those described above can optionally be coupled to an irrigation system. That is, the catheter may include a fluid delivery lumen in the tubular catheter body, with the fluid delivery lumen in fluid communication with electrode segments 14, 16 and distal end 12. When one or more of the flexible electrodes change shape under an applied force, the elongated gap(s) will undergo changes in size and/or shape, thereby affecting the fluid flow therethrough. A cooling fluid, for example, may be pumped in an open flow path through the catheter body to the hollow lumen of the electrode, where it may pass through the gap(s) in the electrode sidewall to the exterior of the electrode, bathing the electrode and adjacent body tissue with cooling fluid. Alternatively, an internal, closed-loop irrigation system using re-circulated cooling fluid as known in the art is also possible. Also, catheters having flexible electrodes can be coupled to an energy source, such as a radio frequency (RF) generator to provide energy needed for tissue ablation. RF signal generators are known and are disclosed, for example, in U.S. Pat. No. 6,235,022.

In one embodiment, and as shown in FIG. 5, distal portion 10 includes a lumen tubing 60 leading distally to a lumen extension member 62 which extends through proximal flexible segment 16 and partially through distal flexible segment 14. Alternatively, lumen extension member 62 extends through proximal flexible segment 16, completely through distal flexible segment 14 and is in fluid communication with exit ports 63 that extend through distal end 12. In a further embodiment, lumen extension member 62 may have any suitable length that does not compromise a flexibility of distal portion 10, such as, for example, a length that is up to approximately 90 percent of a length of distal portion 10. Lumen extension member 62 defines an extended fluid lumen extending through flexible segments 14 and 16, and enables fluid to be channeled from lumen tubing 60 along a longitudinal length of distal portion 10. As such, lumen extension member 62 is in fluid communication with lumen tubing 60. Lumen extension member 62 is configured to provide a substantially constant outflow of fluid along the longitudinal length thereof. Such configurations include openings 64 of sizes and arrangements that may vary from a proximal end 66 to a distal end 68 of lumen extension member 62 to provide a desired (e.g., substantially uniform) irrigation pattern or fluid flow through distal portion 10 and channels 26, as well as lumen shapes and sizes to provide for a substantially constant outflow of fluid.

Lumen extension member 62 can be, and in one embodiment is, fabricated from a suitable biocompatible material including at least one of a polyimide material, a polyether block amide material, a silicone material, and a polyurethane material. In the exemplary embodiment, lumen extension member 62 is fabricated from a material that is substantially similar to the material used to fabricate catheter shaft 20. Alternatively, lumen extension member 62 can be and, in one embodiment, is fabricated from a biocompatible material that is different from the biocompatible material used to fabricate catheter shaft 20. In the exemplary embodiment, lumen extension member 62 is fabricated from a polyimide material.

Lumen extension member 62 may have any suitable cross-sectional shape to enable channeling fluid therethrough. In the exemplary embodiment, lumen extension member 62 has a substantially rounded cross-sectional shape such as one of a circle, an ellipse, and an oval. Moreover, lumen extension member 62 may have any suitable number of portions each having any suitable geometry extending along a longitudinal length of lumen extension member 62. For example, lumen extension member 62 may have a substantially uniform geometry extending along the longitudinal length of lumen extension member 62. Moreover, lumen extension member 62 may have a funnel-shaped geometry extending along the longitudinal length of lumen extension member 62. For example, a funnel-shaped lumen-extension member has a diameter that gradually increases along the longitudinal length of lumen extension member 62 from proximal end 66 to distal end 68. In the exemplary embodiment, lumen extension member 62 includes a proximal portion having a first geometry and a distal portion having a second geometry. Lumen extension member 62 can be formed of, or is partially or entirely coated or lined with, a thermally conductive material to insulate the irrigation fluid, chemicals, therapeutic substances, gels, cooling or heating solutions, and the like from the body or electrode energy.

In one embodiment, a flow constrictor (not shown) is utilized to manipulate the fluid outflow through openings 64. In this embodiment, the flow constrictor decreases a lumen diameter along a longitudinal length of lumen extension member 62 between successive sets of openings 64. Such a flow constrictor can be configured to provide a substantially constant fluid flow through openings 64 along a longitudinal length of lumen extension member 62, when utilized with appropriately sized and shaped openings.

In the exemplary embodiment, openings 64 extend through a sidewall of lumen extension member 62 to enable channeling fluid flow along the longitudinal length of distal portion 10. Each opening 64 may have any suitable configuration. In the exemplary embodiment, each opening 64 has a substantially rounded shape such as a circle, an ellipse, and an oval. Moreover, in the exemplary embodiment, at least one opening 64 has an axis that is substantially perpendicular to the longitudinal length of lumen extension member 62. Furthermore, in the exemplary embodiment, at least one opening 64 has a diameter of approximately 0.05 mm to approximately 0.20 mm. In one embodiment, lumen extension member 62 is fabricated from a material that enables openings 64 to change size and or configuration when member 62 is flexed. Such changes include openings 64 becoming larger or smaller as member 62 flexes and/or openings 64 changing shape from circular to oval or elliptical, or changing shape from oval or elliptical to circular. This embodiment would enable more fluid to flow towards tissue being ablated due to the curvature of distal portion 10 as tissue is contacted.

Figure 8:
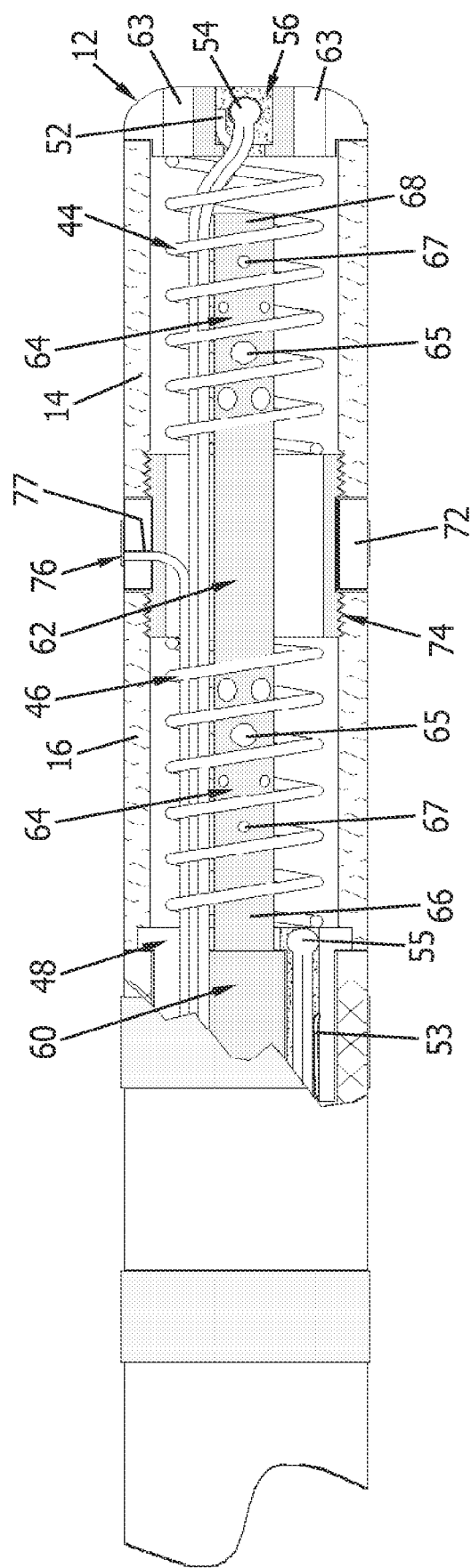
FIG. 8 is a partial cross-sectional view of another embodiment of a distal portion of an ablation catheter similar to the catheter shown in FIG. 6 that has an alternative opening pattern.

In one embodiment, openings 64 include a first set of openings 65 and a second set of openings 67. Openings in first set 65 are larger than openings in second set 67. In one embodiment, second set openings 67 are about half the size of first set openings 65. These differently sized openings 64 allow for a substantially constant fluid flow through openings 64. As shown in FIG. 5, first set of openings 65 are proximal to second set of openings 67 within each flexible electrode 14, 16. FIG. 8 illustrates another configuration of openings 64 in which second set of openings 67 is proximal to the first set of openings 65 within flexible electrode 16 and first set of openings 65 is proximal second set of openings 67 within flexible electrode 14. Alternatively, any pattern of openings could be utilized that provides a substantially constant fluid flow such as first set of openings 65 proximal to second set of openings 67 within flexible electrode 16 and second set of openings 67 proximal to first set of openings 65 within flexible electrode 14, as well as second set of openings 67 proximal to first set of openings 65 within each flexible electrode 14, 16. First set of openings 65 and second set of openings 67 each may include any suitable quantity of openings. For example, first set of openings 65 may include a first quantity of openings, and second set of openings 67 may include a second quantity of openings. In the exemplary embodiment, the first quantity is equal to the second quantity. Alternatively, the first quantity can be and, in one embodiment, is more or less than the second quantity.

In an alternative embodiment, a dedicated lumen extension member (not shown) extends to each flexible segment and to distal end 12 such that a uniform amount and rate of fluid is delivered to each flexible segment 14, 16 and to distal end 12 to provide uniform fluid outflow through channels 26 in each flexible segment 14, 16 and through exit ports 63. Such dedicated lumen extension members can extend through an entire length of catheter 20 or they may each connect to, and extend from, lumen tubing 60. In a further alternative embodiment, no lumen extension member is utilized and lumen tubing 60 ends proximally of proximal flexible segment 16 to allow for increased flexibility of flexible segments 14, 16 and hence distal portion 10. In one embodiment, distal end 68 of lumen extension member 62 is plugged to prevent fluid outflow therefrom. Alternatively, one or more openings can extend through plugged distal end 68 to allow fluid to flow therethrough.

Embodiments of ablation catheters including a distal portion 10 and a lumen extension member 62 facilitate providing a radially directed irrigation pattern that is substantially uniform along a longitudinal length of distal portion 10 when distal portion 10 is in the unflexed, or relaxed state. In addition, lumen extension member 62 provides a varying fluid flow along the longitudinal length of distal portion 10 due to the variations in size of the openings or gaps formed by channels 26 when flexible electrodes 14, 16 are in the flexed position. For example, more fluid flows toward the tissue surface than away from the tissue surface during a procedure due to the gaps becoming more open toward the tissue surface and less open away from the tissue surface.

As seen in FIG. 5, fluid that exits within proximal flexible electrode 16 can flow through tube 40 and exit distal portion 10 through channels 26 that extend through distal flexible electrode 14. As well, fluid that exits within distal flexible electrode 14 can flow through tube 40 and exit distal portion 10 through channels 26 that extend through proximal flexible electrode 16. Alternatively, tube 40 can be plugged so fluid cannot flow therethrough between proximal flexible electrode 16 and distal flexible electrode 14.

Flexible tip electrodes for ablation catheters may be formed and fabricated, for example, according to the following methodology. An exemplary method includes providing a hollow cylindrical electrode, and applying a laser to the cylindrical wall of the electrode to cut through a wall of the electrode. The laser cuts the wall in a pre-determined pattern that may extend helically around the circumference of the electrode wall, or may conform to any of the elongated groove or opening patterns previously described above in the various embodiments. The cuts create channels 26 that are consistently wider in some sections and narrower in other sections. The wider sections allow freedom of movement to narrow or widen channels 26 as previously described, making it possible to shorten an axial length of at least one of flexible electrodes 14, 16 when a force is applied proximally at distal portion 10.

Figure 6:
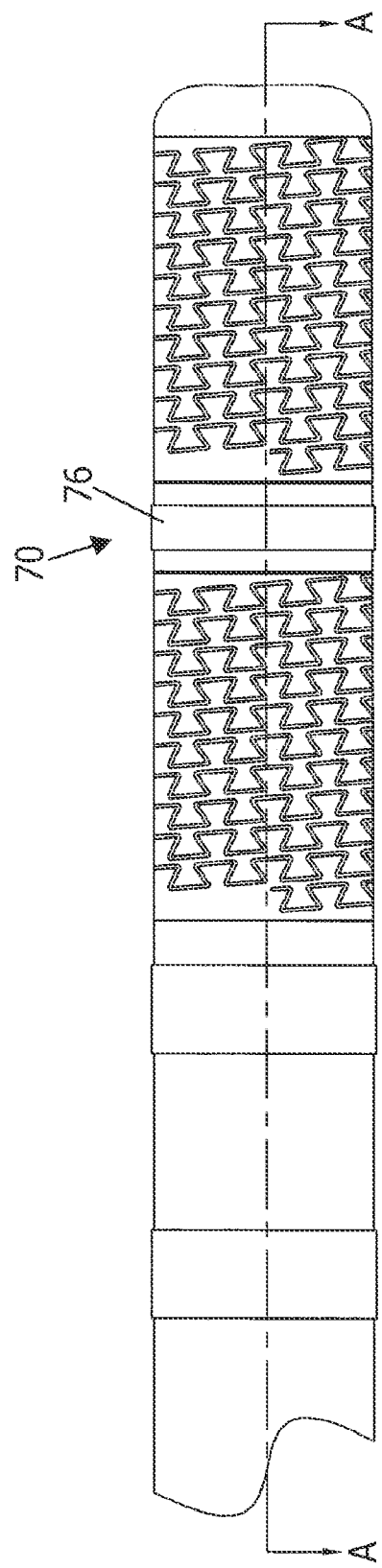
FIG. 6 is a schematic view of a distal portion of an ablation catheter according to a second embodiment of the invention.
Figure 7:
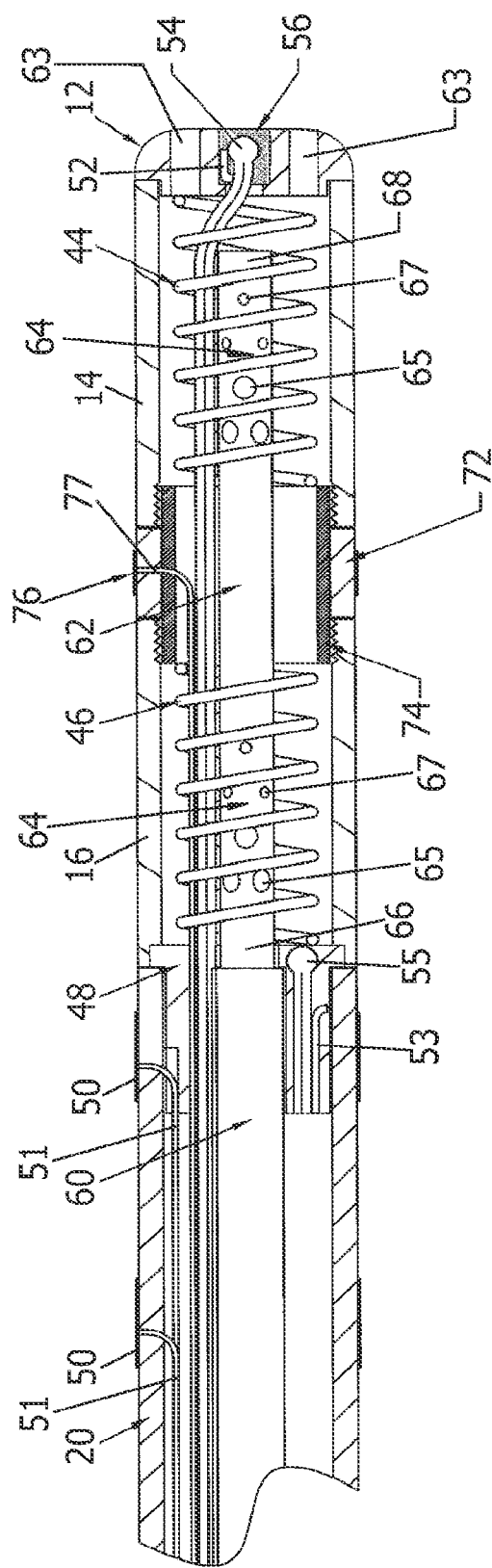
FIG. 7 is a partial cross-sectional view of the distal portion of the ablation catheter shown in FIG. 6.

FIG. 6 is a schematic view of a distal portion 70 of an ablation catheter according to a second embodiment of the present invention. FIG. 7 is a partial cross-sectional view of distal portion 70 of the ablation catheter shown in FIG. 6. FIGS. 6 and 7 differ from FIGS. 1 and 2 in the configurations of intermediate segment 72 and tube 74 and the connection they provide to flexible electrode segments 14, 16. As shown in FIGS. 6 and 7, tube 74 has external threads that engage internal threads of intermediate segment 72 and flexible electrode segments 14, 16, so as to provide a threaded connection. In addition, a band electrode 76 is included on an external surface of intermediate segment 70 and an electrode wire 77 extends to band electrode 76 and provides energy to band electrodes 76. Wire 77 is coupled at its proximal end to an energy source as is well known in the art.

FIGS. 1-8 illustrate a distal portion of an ablation catheter that includes two flexible electrode segments. In other embodiments, there may be three or more flexible electrode segments. Each pair of neighboring flexible electrode segments are separated by an electrically nonconductive segment.

Recent angiographic studies have shown a highly variable cavotricuspid isthmus anatomy with various configurations and topography, which may lead to difficulties in some atrial flutter cases. Placing a long-tipped, rigid 8 mm electrode into pouch-like recesses found in these patients may present technical challenges. The multi-segmented flexible tip catheter design may better enable the electrodes to synchronously maintain tissue contact with the beating heart and also facilitate the creation of a linear lesion. This tip may also be advantageous in ablating within the trabeculated endocardial regions of patients with ventricular tachyarrhythmias, and in ablating the roof lines in atrial fibrillation procedures. It may also be useful when ablating within the coronary sinus.

The many embodiments of flexible electrodes facilitate performing linear ablation procedures. As with typical ablation catheters, a physician can perform mapping using the electrodes, and determine a target site for ablation. Once determined, the physician drags the flexible tip electrode across the target tissue to start ablation while applying energy to the tissue. Because the electrode is flexible, the electrode can be more easily dragged across tissue surfaces having ridges and bumps while keeping constant electrode-to-tissue contact. This is possible because the flexible tip electrode deforms and/or flexes when it is dragged across a tissue surface. The flexible and deformable properties of the flexible tips results in greater electrode-to-tissue surface area than would otherwise be possible with a rigid tip electrode. And because the gaps in the electrode wall allows the electrode to be shortened when pressed tip-down against tissue surface, accidental tissue-perforation is largely avoided if not eliminated.

This written description uses examples to disclose the invention, including the best mode, and also to enable any person skilled in the art to practice the invention, including making and using any devices or systems and performing any incorporated methods. Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A catheter apparatus comprising:
   an elongated body having a distal portion including a sidewall, a distal end, a plurality of flexible segments, and at least one intermediate segment that is less flexible than said flexible segments, wherein adjacent said flexible segments are spaced from each other longitudinally by said at least one intermediate segment, wherein each said flexible segment comprises a sidewall formed of interlocking members, wherein said at least one intermediate segment is shorter than said flexible, segments;
   a lumen extension member having a sidewall and a lumen extending therethrough, said lumen extension member extends beyond a proximal most flexible segment, has a length that does not compromise a flexibility of said distal portion, and is coupled to said distal portion;
   a plurality of openings extending through said lumen extension member; and
   at least one biasing member that resiliently biases at least one flexible segment of said plurality of flexible segments to a pre-determined configuration when no applied force is placed on said distal portion.

2. A catheter in accordance with claim 1 wherein each said flexible segment comprises an electrode and said at least one intermediate segment comprises a non-conductive member.

3. A catheter in accordance with claim 1 wherein said plurality of openings includes a first set of openings and a second set of openings, a size of said openings in said first set being larger than a size of said openings in said second set.

4. A catheter in accordance with claim 1 wherein a size of said openings is configured to provide a substantially constant outflow of fluid along said distal portion.

5. A catheter in accordance with claim 1, wherein said sidewall is provided with gaps formed at least partially therethrough, the gaps outlining alternating interlocking blocks.

6. A catheter in accordance with claim 1, wherein said distal portion is bendable about 40 to about 44 degrees relative to a longitudinal axis of said distal portion.

7. A catheter in accordance with claim 1, wherein said at least one biasing member does not directly contact said at least one flexible segment in an at rest position.

8. A catheter apparatus comprising:
an elongated body having a distal portion including a distal end, a plurality of flexible segments, and at least one intermediate segment that is less flexible than each flexible segment of said plurality of flexible segments, wherein adjacent said flexible segments are spaced from each other longitudinally by said at least one intermediate segment, wherein each said flexible segment comprises a shape memory alloy and a sidewall formed of interlocking members, and wherein said at least one intermediate segment is shorter than said flexible segments;
a lumen extension member having a sidewall and a lumen extending therethrough, said lumen extension member extending at least partially through said distal portion and configured such that said lumen extension member does not compromise a flexibility of said flexible segments; and
at least one biasing member that resiliently biases at least one flexible segment of said plurality of flexible segments to a pre-determined configuration when no applied force is placed on said distal portion,
wherein a plurality of openings extend through said sidewall of said lumen extension member, and wherein said lumen extension member extends beyond a most proximal said flexible segment.

9. A catheter apparatus in accordance with claim 8, wherein said plurality of openings includes a first set of openings and a second set of openings, a size of said openings in said first set being larger than a size of said openings in said second set.

10. A catheter apparatus in accordance with claim 8, wherein a size of said openings is configured to provide a substantially constant outflow of fluid along said distal portion.

11. A catheter apparatus in accordance with claim 8, wherein each said flexible segment is configured to allow shortening of an axial length when a force is applied to said flexible segment.

12. A catheter apparatus in accordance with claim 8, wherein each said flexible segment is coated with at least one of gold and platinum.

13. A distal portion for a catheter, said distal portion comprising:
a plurality of flexible segments, each flexible segment of said plurality of flexible segments comprises an electrode portion having a sidewall comprising interlocking members that impart flexibility to said flexible segments and enable different operating configurations relative to a longitudinal axis,
at least one biasing member that resiliently biases at least one flexible segment of said plurality of flexible segments to a pre-determined configuration when no applied force is placed on said distal portion,
at least one intermediate segment adjacent at least one of said flexible segments, and
a lumen extension member having a sidewall and a lumen extending therethrough, said lumen extension member coupled to said distal portion and extending beyond a proximal most electrode portion.

14. A distal portion in accordance with claim 13, wherein the different configurations include at least one of a resting configuration and a configuration having a changed cross sectional shape.

15. A distal portion in accordance with claim 13, wherein said at least one intermediate segment comprises a non-conductive member.

16. A distal portion in accordance with claim 13, wherein said lumen extension member includes a plurality of openings extending therethrough.

17. A distal portion in accordance with claim 13, wherein said electrode portion is configured to be biased to an extended configuration and allow shortening of its axial length when a force is applied to said electrode portion.

18. A distal portion in accordance with claim 13, wherein said electrode portion comprises a shape memory alloy.

19. A distal portion in accordance with claim 13, wherein said electrode portion is coated with at least one of gold and platinum.

* * * * *